United States Patent [19]
Lane et al.

[11] Patent Number: 4,661,476
[45] Date of Patent: Apr. 28, 1987

[54] SKIN COOLING METHOD

[75] Inventors: James W. Lane, Memphis; Davendra D. Parikshak, Germantown; Carl Kaplan, Memphis, all of Tenn.

[73] Assignee: Plough, Inc., Memphis, Tenn.

[21] Appl. No.: 720,779

[22] Filed: Apr. 8, 1985

[51] Int. Cl.$^4$ ............................................ A61K 31/715
[52] U.S. Cl. ...................................................... 514/60
[58] Field of Search .......................................... 514/60

[56] References Cited

U.S. PATENT DOCUMENTS 3,661,815  5/1972  Smith ................................. 260/17.4
4,159,260  6/1979  Jones et al. ........................ 260/17.4
4,226,232  10/1980 Spence ................................ 128/156

OTHER PUBLICATIONS

Spence, the Chemical Abstracts vol. 94, No. 36400k, 1981.

Primary Examiner—Johnnie R. Brown
Assistant Examiner—Elli Peselel
Attorney, Agent, or Firm—Gerald S. Rosen; Stephen I. Miller; Thomas D. Hoffman

[57] ABSTRACT

There is disclosed a method of cooling overheated skin by applying to the surface thereof a composition comprising on a weight basis about 0.5% to 1.5% hydrolyzed starch-acrylonitrile copolymer sodium salt and water and optional lubricants, dyes, moisturizers, preservatives, and the like.

2 Claims, No Drawings

SKIN COOLING METHOD

BACKGROUND

This invention relates to a method of cooling the surface of skin by applying thereto a topical aqueous gel composition containing a starch-polyacrylonitrile graft copolymer.

Skin surface coolants are particularly useful for applying to the surface of skin that has been overheated by excessive exposure to sun and/or wind, although other causes of elevated skin surface temperatures can be treated by the method of this invention.

Although starch-polyacrylonitrile graft copolymers are known to absorb large amounts of water to form gels and have been used in a variety of applications, they have not heretofore been used in topical skin cooling compositions.

Starch-polyacrylonitrile graft copolymers are generally prepared by reacting starch with acrylonitrile as shown in the following U.S. patents.

Smith, U.S. Pat. No. 3,661,815, issued May 9, 1972 discloses a method of preparing starch-acrylonitrile graft copolymers by reacting corn starch with acrylonitrile in the presence of ceric ammonium nitrate. The resulting products have a mole ratio of starch to acrylonitrile of 1:1 to 1:6. They are converted to an alkali metal carboxylate salt by saponifying the starch-acrylonitrile graft copolymer.

This is the method used to produce the preferred copolymer of this invention.

Duchane, U.S. Pat. No. 3,932,322, issued Jan. 13, 1976, discloses improved alkali metal carboxylate salts of starch-acrylonitrile graft copolymers capable of absorbing, before improvement, in excess of 50 parts by weight aqueous fluids per part of copolymer. The mole ratio of acrylonitrile to starch in the copolymers is 2:1 to 10:1. The improvement is mixing in fumed silica or fumed alumina. This results in improved absorption of saline physiological fluids and reduces dusting.

Gugliemelli et al, U.S. Pat. No. 3,984,361, issued Oct. 5, 1976, disclose a stable gelatinized cationic starch graft copolymer latex. The starch is copolymerized with a cationic vinyl monomer, e.g. acrylonitrile.

Weaver et al, U.S. Pat. No. 3,997,484, issued Dec. 14, 1976, discloses aqueous fluid-absorbing compositions of water-insoluble alkali salts of aqueous alkali saponified gelatinized-starch-polyacrylonitrile graft polymers having starch and polyacrylonitrile mole ratios of 1:1.5 to 1:9. The copolymers are capable of absorbing in excess of 300 parts of water by weight.

Smith, U.S. Pat. No. 4,069,177, issued Jan. 17, 1978, discloses alkali metal carboxylate salts of a starch-polyacrylonitrile graft copolymer in which the mole ratio of starch to acrylonitrile is at least 1:6.

Jones et al, U.S. Pat. No. 4,159,260, issued June 26, 1979, discloses hydrolyzed polyacrylonitrile-starch graft copolymers blended with a quaternary ammonium chloride.

Antholz et al, U.S. Pat. No. 4,221,684, issued Sept. 9, 1980, disclose aqueous fluid-absorbing compositions of copolymers of starch and acrylonitrile of weight ratios of 3:1 to 1:3. The compositions are capable of absorbing about 3000 to 10,000 parts of water by weight.

None of the patents disclose compositions containing the copolymers disclosed therein as being useful for cooling the surface of skin.

BRIEF DESCRIPTION

This invention relates to a method of treating skin to cause cooling and a cooling sensation by applying an effective amount of a topical aqueous gel composition comprising, on a weight basis, about 0.5% to 1.5% of an alkali metal salt of a starch-acrylonitrile graft copolymer and about 75% to 99% water. Although it is possible to practice the invention with a composition containing only the copolymer and water, more preferred compositions can contain lubricants, moisturizers, preservatives, dyes and other conventional additives and excipients used in aqueous topical gel compositions.

The specific graft copolymers used in this invention are those which can absorb over 140 ml of water per gram of copolymer, over 55 ml of a 0.4% sodium chloride solution per gram of copolymer and over 35 ml of synthetic urine per gram of copolymer. In addition the copolymer must form a gel with the absorbed water. The mole ratio of starch to acrylonitrile in suitable graft copolymers is about 1:1 to 1:10.

DETAILED DESCRIPTION

The method of this invention comprises cooling the surface of the skin of a person whose skin has an elevated temperature by applying to the situs a topical aqueous gel composition comprising a hydrolyzed starch-polyacrylonitrile graft copolymer sodium salt and water.

Generally, those in need of such treatment have sunburn or windburn or other conditions which cause the temperature of the surface of the skin to be elevated enough to cause discomfort. The method of this invention helps ease the discomfort by cooling the surface of the skin. The composition is applied as frequently as needed in amounts effective to achieve the desired cooling. Thus, for example, if one is at the beach and becomes sunburned, application of the topical aqueous gel composition used in the method of this invention to the sunburned portion of the skin gives a cooling effect along with a drop in surface temperature.

Although it is preferred to apply the cooling composition to sunburned or windburned skin, other conditions causing elevated temperature of the skin such as very hot weather or long exposure to the sun of well tanned skin, are amenable to treatment by the method of this invention.

The starch-acrylonitrile graft copolymer most preferred for use in this invention is WATER-LOCK TM A-100 available from Grain Processing Corporation, Muscatine, Iowa. The copolymer is a hydrolyzed starch-polyacrylonitrile graft copolymer sodium salt. Because formation of the salt is a hydrolysis reaction, the nitrile is converted to acids and amides. The copolymer thus chemically is starch containing grafted side chains of sodium polyacrylate-polyacrylamide copolymers. When referring to the polymer, it will be designated hydrolyzed starch-polyacrylonitrile graft copolymer sodium salt. The specific preferred copolymer has a specific gravity greater than 1, a maximum of 6% volatiles by weight, swells in water to form a gel but is essentially water insoluble. It is an odorless light tan granular powder. It is characterized as having a fluid uptake of at least 140 ml water per gm of polymer, at least 55 ml of an aqueous 0.4% sodium chloride solution per gram of polymer and at least 35 ml of synthetic urine per gram of polymer. The polymer is manufactured by the processes disclosed in either or both of U.S.

Pat. Nos. 3,661,815 and 4,159,260, both of which are incorporated herein by reference.

Other hydrolyzed starch-acrylonitrile graft copolymer salts, particularly alkali metal salts such as the potassium salt (WATER-LOCK TM B), as well as quaternary ammonium salts, and other hydrolyzed starch-acrylonitriles of the WATER-LOCK TM series, i.e. A-120, A-200, A-220, B-100, B-204, L or G are also suitable for use in this invention.

Other similar starch-acrylonitrile graft copolymers such as SUPER-SORB TM available from Super Absorbent Company, Lumberton, N.C. are also suitable for use in this invention. Any other starch-acrylonitrile graft copolymer or a salt thereof which forms a gel upon absorption of water can be used in this invention.

The topical aqueous gel compositions useful in this invention comprises from about 75-99% water, by weight, and about 0.5 to 1.5% of a hydrolyzed starch-acrylonitrile graft copolymer sodium salt, by weight. Additives and excipients can also be present, e.g. on a weight basis, propylene glycol, about 2-6%; preservatives (parabens) about 0.10 to 0.25%; aloe, about 0.03 to 0.04%; benzophenone-4, about 0.04 to 0.06%; antimicrobial (imidazolidinyl urea) about 0.05 to 0.15% and dyes, less than 0.001%. Other functionally equivalent additives as well as perfumes and the like can be used in the formulation if desired.

The following examples illustrate this invention.

EXAMPLE 1

Preparation of Composition

A composition with the following formulation is prepared:

| Ingredients | Percent by weight |
|---|---|
| Propylene glycol | 5.00000 |
| Methyl paraben | 0.20000 |
| Aloe powder | 0.03500 |
| WATER LOCK TM A-100 | 0.90000 |
| Benzophenone-4 | 0.05000 |
| Imidazolidinyl Urea | 0.10000 |
| F.D. and C. Brilliant Blue No. 1 | 0.00074 |
| Water | 93.71426 |
| Total | 100.00000% |

Preparation

1. Into a suitable reaction vessel equipped with a mixer add the propylene glycol then add the methylparaben slowly with mixing until dissolved, then add the aloe slowly with mixing. When uniformly dispersed, slowly add the WATER-LOCK A-100 and mix until uniformly dispersed. Maintain continuous mixing until used in step 5.
2. Add water (92.9750%) to a jacketed tank equipped with a counter-rotary agitator. Begin mixing at ambient temperature and slowly add the benzophenone-4 and the imidazolidinyl urea, mix until completely dissolved.
3. Add the remaining water to a suitable reaction vessel equipped with a propeller mixer and add slowly, with mixing, the F.D.&C. Blue #1. Mix until dissolved.
4. Add, while mixing, the solution of step 3 to the solution of step 2. Continue mixing until uniformly blended.
5. While rapidly mixing the aqueous mixture of step 4, very slowly add the dispersion of step 1. Continue mixing until uniform and a soft blue gel forms.
6. Mill the gel of step 5 in a colloid mill set at #10 and recover the product.

EXAMPLE 2

Apply product of Example 1 to the sunburned portion of the skin of people with a sunburn. A cooler and more comfortable feeling occurs.

We claim:

1. A method of treating skin overheated by exposure to heat, sun or wind to cause cooling thereof and a cooling sensation comprising applying to the surface of such overheated skin an amount effective to cause cooling and a cooling sensation of said skin of a topical aqueous gel composition comprising, on a weight basis, about 75 to 99% water, about 0.5 to 1.5% of a hydrolyzed starch-polyacrylonitrile graft copolymer salt, about 2 to 6% propylene glycol, about 0.10 to 0.25% paraben preservatives, about 0.03 to 0.04% aloe, about 0.04 to 0.06% benzophenone-4, about 0.05 to 0.15% imidazolidinyl urea and up to 0.001% dyes.

2. The method of claim 1 wherein the composition applied is:

| Ingredients | Percent by weight |
|---|---|
| Propylene glycol | 5.00000 |
| Methyl paraben | 0.20000 |
| Aloe powder | 0.03500 |
| Hydrolyzed starch-polyacrylonitrile graft copolymer sodium salt | 0.90000 |
| Benzophenone-4 | 0.05000 |
| Imidazolidinyl Urea | 0.10000 |
| F.D. & C. Brilliant Blue No. 1 | 0.00074 |
| Water | 93.71426 |

* * * * *